United States Patent [19]
Koike et al.

[11] Patent Number: 5,696,247
[45] Date of Patent: Dec. 9, 1997

[54] METHOD FOR PRODUCING ALKYLGLYCOSIDE

[75] Inventors: Toyomi Koike; Kazunori Aizawa; Hiroshi Nagumo, all of Wakayama, Japan

[73] Assignee: Kao Corporation, Tokyo, Japan

[21] Appl. No.: 590,439

[22] Filed: Jan. 23, 1996

[30] Foreign Application Priority Data

Feb. 1, 1995 [JP] Japan ................................. 7-037544

[51] Int. Cl.$^6$ ............................ C07G 3/00; C07H 15/04
[52] U.S. Cl. ........................ 536/18.6; 536/18.5; 536/127
[58] Field of Search ................... 536/18.5, 18.6, 536/127

[56] References Cited

U.S. PATENT DOCUMENTS

| | | | |
|---|---|---|---|
| 4,393,203 | 7/1983 | Mao et al. | 536/124 |
| 4,465,828 | 8/1984 | Rau et al. | 536/18.6 |
| 4,762,918 | 8/1988 | McDaniel, Jr. et al. | 336/127 |
| 4,898,934 | 2/1990 | Lueders et al. | 536/18.6 |
| 4,990,605 | 2/1991 | Lueders | 536/18.5 |
| 5,079,350 | 1/1992 | Fujita et al. | 536/18.6 |
| 5,374,716 | 12/1994 | Biermann et al. | 536/18.6 |
| 5,420,262 | 5/1995 | Schmidt | 536/18.5 |
| 5,519,124 | 5/1996 | McCurry, Jr. et al. | 536/18.5 |

FOREIGN PATENT DOCUMENTS

| | | |
|---|---|---|
| 0132043 | 1/1985 | European Pat. Off. . |
| 0 513 813 | 11/1992 | European Pat. Off. . |
| WO 94/24139 | 10/1994 | WIPO . |

*Primary Examiner*—John Kight
*Assistant Examiner*—Friedrich N. Burnett
*Attorney, Agent, or Firm*—Oblon, Spivak, McClelland, Maier & Neustadt, P.C.

[57] ABSTRACT

A method for producing an alkylglycoside by a reaction of a saccharide and a monohydric alcohol, the method comprising the steps of carrying out the reaction of the saccharide and the monohydric alcohol; adjusting a reaction mixture containing an unreacted monohydric alcohol and an alkylglycoside produced to a pH of 2 to 6.5; and removing the unreacted monohydric alcohol from the reaction mixture by distillation to obtain the alkylglycoside, wherein decoloration treatment may be carried out before removing the unreacted monohydric alcohol.

14 Claims, No Drawings

METHOD FOR PRODUCING ALKYLGLYCOSIDE

BACKGROUND OF THE INVENTION

1. Field of the Invention

The present invention relates to a method for producing an alkylglycoside useful as a surfactant or as an intermediate in the synthesis thereof. Specifically, it relates to a method for producing an alkylglycoside having a good color (hue) and a low odor.

2. Discussion of the Related Art

Alkylglycosides, sugar-derived surfactants, have lately attracted increasing attention because they are less irritating and because it is known that though alkylglycosides are nonionic surfactants, they not only give stable foam themselves but also help other anionic surfactants make stable foam.

Alkylglycosides have novel, notable features as mentioned above, but their production presents a number of problems. The largest problem is that the color and odor of alkylglycosides are liable to deteriorate during various operations in production.

In order to prevent deterioration in color during the production, preventive measures taken in the step of reacting an alkylglycoside with an alcohol (hereinafter simply referred to as "the reaction step") have been proposed. Since deterioration in color is significant in the step of separating the alkylglycoside from unreacted alcohol (hereinafter simply referred to as "the separation step") due to high viscosity and poor thermal stability of alkylglycosides, it has been proposed to add a viscosity reducing agent during this step. These preventive measures, however, have not yet succeeded in providing alkylglycosides having a satisfactory color.

As an alternative method to reduce the color of, alkylglycoside compositions, a method has been studied, which includes contacting an alkylglycoside compositions containing color humin having a conjugated unsaturated bond with hydrogen or a hydrogen source and recovering light colored alkylglycoside compositions. Although a color improving effect could be achieved to some extent by this method, the degree of improvement has not achieved a sufficient level. Also, this method necessitates equipment for hydrogenation and expensive alkali metal hydrides as a hydrogen source, and therefore is not suitable for production on an industrial scale. It has also been proposed to bleach a resulting alkylglycoside with hydrogen peroxide and a sulfur dioxide source. This method could not provide a radical solution to the problems, because although deterioration in color is prevented, new problems such as odor deterioration and poor storage stability arise.

In Japanese Patent Laid-Open No. 6-192284, a method to reduce the color of alkylglycoside compositions is disclosed, in which the alkylglycoside product is treated with an alkali to have a pH of 10 to 14 and maintained at a temperature of 60° to 120° C. for 2 or more hours, and the unreacted alcohol is removed by distillation at pH 7 to 9. In this method, there is a problem that the reaction product is colored during the alkali treatment and alcohol distillation, requiring a great deal work for decoloration in water after alcohol removal.

In WO94/24139, proposed is a method in which alcohol is removed by distillation after an oxide, such as magnesium oxide, is added to the product of the reaction between a saccharide and an alcohol, preferably at pH 3 to 4. This method also presents a problem for industrial in that the metal oxide, an essential substance of this method, is not soluble in water and causes turbidity, necessitating a filtration process to give a commercially acceptable product.

SUMMARY OF THE INVENTION

As mentioned above, various approaches have been tried for the production of alkylglycosides, but further improvements are still needed to solve problems such as insufficient decoloration and unpleasant odor.

In order to solve the above problems, it is an object of the present invention to provide an improved method for producing alkylglycosides with favorable color and little odor.

As a result of intensive studies, the present inventors found that adjusting a reaction mixture containing an unreacted alcohol or phenol and an alkylglycoside produced to a pH of 2 to 6.5 and distilling off the excess alcohol or phenol at this pH enable the production of alkylglycosides with favorable dolor, and have completed the present invention.

Namely, the present invention is mainly concerned with:

(1) A method for producing an alkylglycoside by a reaction of a saccharide and a monohydric alcohol, the method comprising the steps of:

carrying out the reaction of the saccharide and the monohydric alcohol;

adjusting a reaction mixture containing an unreacted monohydric alcohol and an alkylglycoside produced to a pH of 2 to 6.5; and removing the unreacted monohydric alcohol from the reaction mixture by distillation to obtain the alkylglycoside;

(2) A method for producing an alkylglycoside by reacting a saccharide and a monohydric alcohol, the method comprising the steps of:

carrying out the reaction of the saccharide and the monohydric alcohol;

subjecting a reaction mixture containing an unreacted monohydric alcohol and an alkylglycoside produced to decoloration treatment;

adjusting the reaction mixture containing an unreacted monohydric alcohol and an alkylglycoside produced to a pH of 2 to 6.5; and removing the unreacted monohydric alcohol from the reaction mixture by distillation;

(3) The method described in (1) or (2) above, wherein further decoloration treatment is carried out after the unreacted monohydric alcohol is removed by distillation;

(4) The method described in (2) or (3) above, wherein the decoloration treatment is selected from the group consisting of hydrogen peroxide treatment, sodium hypochlorite treatment and hydrogenation treatment;

(5) The method described in any one of (1) to (4) above, wherein the alkylglycoside produced is represented by the following formula (I):

$$R_1(OR_2)_xG_y \qquad (I)$$

wherein $R_1$ represents a linear or branched alkyl group having 1 to 22 carbon atoms, a linear or branched alkenyl group having 2 to 22 carbon atoms, or a linear or branched alkylphenyl group having 7 to 22 carbon atoms; $R_2$ represents an alkylene group having 2 to 4 carbon atoms; G represents a residue derived from a reducing saccharide having 5 to 6 carbon atoms; X is a molar addition number of alkylene oxide group, having an average value of from 0 to 5; y is condensation degree of reducing saccharide having an average value of from 1 to 10;

(6) The method described in any one of (1) to (5) above, wherein the monohydric alcohol is a linear or branched, saturated or unsaturated alcohol having 1 to 22 carbon atoms, or an alkylene oxide addition product thereof, or a mixture thereof;

(7) The method described in (5) above, wherein $R_1$ is a linear or branched alkyl group having 8 to 16 carbon atoms, and the saccharide is glucose;

(8) The method described in (1) or (2) above, wherein an acidic substance or a basic substance is used to adjust the reaction mixture to a pH of from 2 to 6.5, the acidic substance or the basic substance being soluble in the reaction mixture when used in an amount required to adjust the pH of the reaction mixture within the above range;

(9) The method described in (8) above, wherein the acidic substance is selected from the group consisting of p-toluenesulfonic acid, sulfuric acid, phosphoric acid, lactic acid, acetic acid, glycolic acid and hydrochloric acid, and wherein the basic substance is selected from the group consisting of NaOH, KOH, $NH_3$, $Na_2CO_3$, $NaHCO_3$, lower alkyl amines, and lower alkanol amines;

(10) The method described in (4) above, wherein the hydrogen peroxide treatment is carried out at a pH of from 7 to 13;

(11) The method described in (4) above, wherein the sodium hypochlorite treatment is carried out at a pH of from 7 to 13;

(12) The method described in (4) above, wherein the hydrogenation treatment is carried out at a pH of not lower than 8; and

(13) The method described in any one of (10) to (12) above, wherein pH is adjusted with a basic substance selected from the group consisting of NaOH, KOH, $Na_2CO_3$, $NaHCO_3$, $NH_3$, lower alkanol amines, lower alkyl amines, and strongly basic ion exchange resins.

The present invention will be described in detail below.

DETAILED DESCRIPTION OF THE INVENTION

Any known method may be employed in the reaction step of the present invention as long as an alkylglycoside can be obtained. For example, the following methods may be employed: a method wherein a reaction is carried out by directly contacting a saccharide with an alcohol or phenol in the presence of an acid catalyst; and a method wherein an alkylglycoside having a lower alkyl group is first obtained by the reaction between a saccharide and a lower alcohol, such as methanol, ethanol, propanol and butanol, which is then reacted with a higher alcohol.

Any saccharides may be used as the starting saccharide of the present invention. For example, monosaccharides, oligosaccharides, polysaccharides and mixtures thereof may be used. Examples of the monosaccharides used in the present invention include aldoses, such as allose, altrose, glucose, mannose, gulose, idose, galactose, talose, ribose, arabinose, xylose, and lyxose. Examples of oligosaccharides include maltose, lactose, sucrose, and maltotriose. Examples of polysaccharides include hemicellulose, inulin, dextrin, dextran, xylan, starch and hydrolyzed starch.

Among the above examples, reducing saccharides having not more than 6 carbon atoms, such as glucose, mannose, talose, and galactose, are preferred in terms of performance (foaming ability, detergency), with a particular preference being given to glucose.

Any monohydric alcohols are used in the present invention. Examples include a linear or branched, saturated or unsaturated alcohol having 1 to 22 carbon atoms, alkylene oxide addition product of linear or branched, saturated or unsaturated alcohol having 1 to 22 carbon atoms, and a mixture thereof, with a preference given to a compound represented by the following formula (II) in terms of performance (foaming ability, detergency) and productivity:

$$R_3(OR_4)_nOH \qquad (II)$$

wherein $R_3$ represents a linear or branched alkyl or alkenyl group having 1 to 22 carbon atoms; $R_4$ represents an alkylene group having 2 to 4 carbon atoms; and n is a number having an average value of 0 to 5.

Here, $R_3$ is a linear or branched alkyl or alkenyl group having 1 to 22 carbon atoms, preferably a linear or branched alkyl group having 8 to 16 carbon atoms, more preferably a linear alkyl group having 10 to 14 carbon atoms. $R_4$ is an alkylene group having 2 to 4 carbon atoms, preferably an ethylene group. n is a number having an average value of 0 to 5, preferably 0 to 1, more preferably 0.

Specific examples of the above monohydric alcohol include methanol, ethanol, isopropyl alcohol, butanol, hexanol, heptanol, 2-ethylhexanol, decyl alcohol, dodecyl alcohol, tetradecyl alcohol, hexadecyl alcohol, octadecyl alcohol, oleyl alcohol, icosyl alcohol, coconut alcohol, oxoalcohol, and Guerbet alcohol. Also ethylene oxide addition products of the above alcohols are exemplified, the molar addition number of ethylene oxide being 1 to 5. Among the above examples, decyl alcohol, dodecyl alcohol, and tetradecyl alcohol are preferred in terms of performance. One or more kinds of the above monohydric alcohols may be used as long as a desired effect can be achieved.

Examples of the phenols used in the present invention include alkyl phenols, such as nonyl phenol and dodecyl phenol, and ethylene oxide addition products of these phenols can also be used, the molar addition number of ethylene oxide being 1 to 5. Among them, nonyl phenol and dodecyl phenol are preferred in terms of performance.

The above-mentioned alcohols and phenols can be obtained from suppliers. The alkylene oxide addition products of monohydric alcohols and phenols can be obtained by conventional methods. Specifically, they can be prepared by addition reaction of an alkylene oxide to a monohydric alcohol or a phenol in the presence of KOH or NaOH.

The reaction method which is employed in the reaction step of the present invention is not limited as mentioned above. One embodiment of the present invention is described below.

A starting alcohol or phenol, a saccharide and a catalyst are placed in a reactor. Monohydric alcohol or phenol is used in an amount of 2 to 10 mol, preferably 3 to 7 mol to 1 mol of saccharide. The amount of alcohol or phenol is preferably not lower than 2 mol in view of conversion, and not higher than 10 mol in technical and economic viewpoints. Any reactors can be used as long as inside of the reactor can be depressurized. Examples include a SUS-reactor and a GL-reactor.

Any known catalysts can be used in the present invention as long as they are for dehydration reaction. Examples include p-toluenesulfonic acid, sulfuric acid, phosphoric acid, and strongly acidic ion exchange resins (NAPHION, AMBERLITE, and DIAION). These substances can be obtained from suppliers. One or more kinds of these substances may be used. Among them, a preference is given to p-toluenesulfonic acid because of less coloration and less odor upon reaction. The amount of a catalyst added is not particularly restricted. In order to inhibit the coloration of the reaction mixture, 0.001 to 0.01 mol, preferably 0.002 to 0.005 mol of a catalyst is added per 1 mol of a saccharide.

The starting materials and a catalyst are placed in a reactor, and dehydration is carried out by heating and depressurizing the reactor. The reaction temperature is in the range of from 80° to 150° C., preferably 90° to 120° C. A temperature of 80° C. or higher is preferred in terms of reaction rate, and a temperature of 150° C. or lower is preferred in terms of inhibition of coloration. The pressure is reduced by 5 to 100 mmHg, preferably 20 to 60 mmHg. A reduction of not smaller than 5 mmHg is preferred in terms of equipment and a reduction of not larger than 100 mmHg is preferred in terms of dehydration efficiency. In order to efficiently remove the water formed in the reactor, nitrogen may be introduced into the reactor. The amount of nitrogen introduced into the reactor is not limited, and it may be in the range of 0.1 to 1N m³/hour per 1 ton of the reaction mixture charged in the reactor. The reaction time depends upon the amounts of the starting materials. Therefore, the reaction may be discontinued at any time when it is known from the consumption amount of the starting materials or the amount of the product that the reaction has been almost completed.

After the completion of the reaction, the pressure in the reactor is normalized. Here, in order to prevent saccharide from being further condensed, the reaction mixture containing an acid catalyst may be neutralized to a pH of 6 to 8 or may be adjusted to a pH suitable for the subsequent processes by the addition of a basic substance. When a precipitate (polysaccharide by-products and unreacted saccharide) comes out, it may be filtered off according to necessity. Thus, a reaction mixture containing an unreacted alcohol or phenol and an alkylglycoside product is obtained. Any basic substances may be used for neutralizing an acid catalyst, including NaOH, KOH, $Na_2CO_3$, $NaHCO_3$, $NH_3$, lower alkanol amines, lower alkyl amines, and strongly basic ion exchange resins, with a preference being given to NaOH and KOH in terms of economy, solubility and handiness. NaOH or KOH is preferably used as an aqueous solution to improve handiness.

The alkylglycoside in the present invention is not limited. Those represented by the following formula (I) are preferred because they are useful as surfactants and intermediates in the synthesis of surfactants:

$$R_1(OR_2)_xG_y \qquad (I)$$

wherein $R_1$ represents a linear or branched alkyl group having 1 to 22 carbon atoms, a linear or branched alkenyl group having 2 to 22 carbon atoms, or a linear or branched alkylphenyl group having 7 to 22 carbon atoms; $R_2$ represents an alkylene group having 2 to 4 carbon atoms; G represents a residue derived from a reducing saccharide having 5 to 6 carbon atoms; X is a molar addition number of alkylene oxide group, having an average value of from 0 to 5; y is condensation degree of reducing saccharide having an average value of from 1 to 10.

Here, $R_1$, $R_2$ and x can be controlled by changing the starting monohydric alcohols and phenols, and G, by changing the type of saccharides. The value of y can be controlled by changing the molar ratio of the starting monohydric alcohol or phenol to the saccharide and reaction conditions. The value of y can be confirmed by determining the distribution of condensation degrees of the product by GPC, or by obtaining the ratio of the number of protons derived from $R_1$ to that derived from G by NMR analysis. The value of y is in the range of from 1 to 10, preferably 1 to 3, more preferably 1.2 to 1.6.

Next, in the separation step, the alcohol or phenol is removed from the reaction mixture. Decoloration may be carried out before the removal of alcohol or phenol, because the color of the alkylglycoside product can further be improved by this treatment. The method for decoloration treatment is not limited, and any known decoloration treatments, such as hydrogen peroxide treatment, sodium hypochlorite treatment and hydrogenation treatment, may be used.

The hydrogen peroxide treatment may be carried out as follows: The pH of the reaction mixture is adjusted to 7 to 13, preferably 8 to 12. The pH adjustment to the above range may or may not be preceded by neutralization of the acid catalyst. The pH of the reaction mixture is preferably not lower than 7 in terms of decoloration efficiency, and not higher than 13 to prevent re-coloration. In the present specification, "the pH of the reaction mixture" means the pH value for a 5% by weight dilution of the reaction mixture diluted with distilled water. Incidentally, pH is gradually lowered during the treatment with $H_2O_2$. The addition amount of hydrogen peroxide is 0.05 to 1.0 parts by weight, preferably 0.1 to 0.5 parts by weight based upon 100 parts by weight of the reaction mixture (10 to 80 parts by weight of alkylglycoside), the amount generally being dependent on the desired color for the alkylglycoside product. After this amount of hydrogen peroxide is added, the reaction mixture is stirred at a temperature of 40° to 150° C., preferably 50° to 90° C., for 10 minutes to 8 hours for decoloration. The temperature for decoloration is preferably not lower than 40° C. in terms of decoloration efficiency, and not higher than 150° C. to prevent color deterioration caused by high temperature.

The sodium hypochlorite treatment may be carried out as follows: The reaction mixture is adjusted to a pH of 7 to 13, preferably 8 to 12. It is preferable to adjust the pH of the reaction mixture to not lower than 7 in view of decoloration efficiency, and to not higher than 13 to prevent re-coloration of the product. The amount of sodium hypochlorite to be added is 0.01 to 0.5 parts by weight, preferably 0.05 to 0.3 parts by weight based upon 100 parts by weight of the reaction mixture (10 to 80% by weight of alkylglycoside), the amount being generally dependent on the desired color for the alkylglycoside product. After addition of this amount of sodium hypochlorite, the reaction mixture is stirred at a temperature of 40° to 150° C., preferably 50° to 90° C., for 10 minutes to 8 hours for decoloration. The temperature for decoloration is preferably not lower than 40° C. in terms of decoloration efficiency, and not higher than 150° C. to prevent color deterioration caused by high temperature.

The-hydrogenation treatment may be carried out, for example, according to the method disclosed in Japanese Patent Laid-Open No. 1-290692 in which the reaction mixture is directly contacted with hydrogen or a hydrogen source. Specifically, the reaction mixture is contacted with hydrogen at a pressure of 1 to 100 atm and a temperature of 150° to 250° C. in the presence of a catalyst containing Ni, Pt, Pd, etc. When sodium borohydride is used as a hydrogen source, the reaction mixture is adjusted to a pH of not lower than 8, and sodium borohydride is added in an amount of 0.01 to 1.0 parts by weight based upon 100 parts by weight of the reaction mixture. After addition of sodium borohydride, the reaction mixture is stirred at a temperature of 20° to 75° C. for 1 to 100 hours for decoloration.

Examples of the basic substances used for pH adjustment in each of the above decoloration treatments include those used for the neutralization of the acid catalyst. In terms of decoloration efficacy, NaOH and KOH are preferred. It is preferred in terms of handiness to use NaOH or KOH as an aqueous solution. The production methods of the substances used in the decoloration treatment, i.e., hydrogen peroxide, sodium hypochlorite, hydrogen, hydrogenation catalyst, and sodium borohydride are not limited. Using those commercially available is economically advantageous.

The separation step of the present invention will be described below. The pH of the reaction mixture obtained as mentioned above, with or without decoloration treatment, is adjusted to 2 to 6.5, preferably 3 to 6, more preferably 3.5 to 5. Here, "pH of the reaction mixture" means the pH of a 5% by weight dilution of the reaction mixture diluted with distilled water. In the separation step, pH of the reaction mixture is preferably not lower than 2 to inhibit further condensation of saccharides, and not higher than 6.5 to obtain a product with desirable color. pH can be adjusted with an acidic or basic substance. The amount of the acidic or basic substance to be added to the reaction mixture is not limited as long as a desired pH can be achieved.

Any acidic substance may be used here as long as they can be dissolved in the reaction mixture to a desired extent. Examples of the acidic substances include p-toluenesulfonic acid, sulfuric acid, phosphoric acid, lactic acid, acetic acid, glycolic acid, and hydrochloric acid. In terms of the color of the product separated, a preference is given to p-toluenesulfonic acid. The basic substances used here are not limited as long as they can be dissolved in the reaction mixture to a desired extent. Examples of the basic substances include NaOH, KOH, NH$_3$, Na$_2$CO$_3$, NaHCO$_3$, lower alkyl amines, and lower alkanol amines. Among them, NaOH and KOH are economically preferred.

Before distillation of alcohol or phenol, various compounds may be added for pH adjustment or other purposes. However, addition of a low soluble metal oxide such as magnesium oxide causes turbidity of the reaction mixture, which necessitates filtration to give a commercially acceptable product. This additional filtration process increases the production cost and decreases the yield. Therefore, the use of metal oxide is undesirable for the production on industrial scale.

The reaction mixture adjusted to a desired pH as mentioned above is subjected to distillation to remove an unreacted alcohol or phenol. The distillation may be carried out according to a known method, preferably at a low temperature in order to prevent the alkylglycoside product from getting color and odor. It is preferred to carry out distillation under a reduced pressure because distillation at a lower temperature becomes possible. The degree of depressurization depends on the type of alcohol or phenol to be distilled off. For example, an alcohol having 10 to 14 carbon atoms is distilled at a pressure of 0.01 to 10 mmHg, preferably 0.1 to 1 mmHg. The temperature during distillation is 100° to 200° C., preferably 130° to 170° C. Distillation apparatuses are not limited, and any known apparatuses may be used. Specific examples include thin-film evaporator, batch-type evaporator, and continuous one. It is preferred to use an evaporator which can avoid long-term exposure of the reaction product to heat. In this respect, a thin-film evaporator is prepared. The thickness of the thin-film is preferably not more than 5 mm, more preferably not more than 2 mm. The types of thin-film evaporator include down-flow liquid film type, up-flow liquid film type, wiped film type, and drum evaporator. The alcohol or phenol in the reaction mixture is distilled away to a level of not higher than 5% by weight of the reaction mixture, preferably to a level of not higher than 2% by weight of the reaction mixture to give an alkylglycoside.

The color of the alkylglycoside thus obtained is evaluated as follows: 40% aqueous solution of the alkylglycoside is prepared, and the color of the aqueous solution is visually compared with the APHA color standard.

The alkylglycoside product obtained as above may further be subjected to decoloration treatment. The method used for this decoloration treatment is not limited. For example, the known methods as described above, such as hydrogen peroxide treatment, sodium hypochlorite treatment, and hydrogenation treatment, may be used.

According to the present invention, an alkylglycoside having a good color and no odor can be obtained by very simple procedures without using an expensive decoloring agent.

EXAMPLES

The present invention is hereinafter described by means of the following working examples and comparative examples, but the present invention is not limited by them.

Example 1

In a 20-liter SUS-reactor, 9497 g (60.0 mol) of decyl alcohol, 2700 g (15.0 mol) of anhydrous glucose, and 14.3 g (0.075 mol) of p-toluenesulfonic acid monohydrate were placed, and stirred. After the mixture was heated to 95° C., the pressure in the reaction system was adjusted to 40 mmHg to start dehydration. During the dehydration, nitrogen was introduced into the reactor at 200 mL/min to efficiently remove the water formed. The mixture was further heated. When the temperature reached 110° C., sampling was conducted every 1 hour to know the amount of glucose consumption. Dehydration was continued until the conversion calculated from the glucose consumption became 96% or higher. After the completion of the reaction, the pressure was normalized and the catalyst was neutralized by adding 17.5 g (0.21 mol) of 48% by weight of NaOH aqueous solution. By products formed during the reaction, such as polysaccharides, and unreacted glucose, were removed by filtration. The color of the solution was evaluated as APHA 300 to 400.

The conversion was calculated based upon the amount of glucose consumption in the reaction mixture. Specifically, the reaction mixture was filtered and the amount of solid glucose filtered out was measured. The difference in glucose amount in each sample from the starting amount is regarded as the amount of glucose consumption at the time of sampling. The conversion is calculated using the following Equation 1:

$$\text{Conversion (\%)} = \frac{\text{Glucose consumption}}{\text{Starting amount of glucose}} \times 100 \qquad (1)$$

The color of the product was expressed by APHA. APHA is in accordance with Hazen unit of JIS K0071-1993. The specific procedures will be described below.

In 100 mL of hydrochloric acid, 1.25 g of potassium chloroplatinate and 1.00 g of cobalt chloride were dissolved, to which water was added to make a total volume of one liter. After the solution was adjusted to have an absorbance in the range shown in Table 1 using a spectrophotometer, it was used as the standard matching stock solution.

TABLE 1

| Wave length (nm) | Absorbance |
|---|---|
| 430 | 0.110–0.120 |
| 455 | 0.130–0.145 |
| 480 | 0.105–0.120 |
| 510 | 0.055–0.065 |

APHA of this stock solution is defined to be 500. The APHA value of each dilution of the stock solution is calculated so that the multiplicative product of dilution ratio by APHA value becomes 500, i.e., the APHA value of 2-time dilution is 250; that of 5-time dilution, 100; and so on. A sample taken from the reaction mixture is visually compared with the series of APHA standard matching solutions thus prepared, and the APHA standard matching solution having the most similar color to the sample is selected. The color of the sample is expressed by the APHA value of the standard matching solution thus selected.

In a 1-liter reactor, 500 g of the reaction mixture (containing alkylglycoside in an amount of about 30% by weight; hereinafter referred to as "the reaction mixture of Example 1") was placed and stirred. After the reaction mixture of Example 1 was heated to 70° C., 1.00 g (0.012 mol) of 48% by weight NaOH aqueous solution and 2.86 g of 35% by weight $H_2O_2$ aqueous solution were added and stirred at 70° C. for 3 hours for decoloration. During the decoloration treatment, the reaction mixture was sampled at several points. The sample was diluted to a concentration of 5% by weight and the pH of the dilution was determined. As a result, the pH of the reaction system during the decoloration treatment was in the range of from 11.5 to 8.5.

After the completion of the decoloration treatment, the pH of the reaction mixture was adjusted with 7.61 g (0.012 mol) of 30% by weight p-toluenesulfonic acid monohydrate decyl alcohol solution (hereinafter referred to as "acid solution"). The color of the reaction mixture was APHA 70 to 80, indicating that the reaction mixture had been decolored. The pH of the reaction mixture was 3.0. The reaction mixture was further diluted with distilled water to a concentration of 5% by weight, and the pH of the resulting suspension was 3.5. Unless otherwise specified, pH in the following examples was determined after a subject liquid was diluted with distilled water to a concentration of 5% by weight.

Unreacted alcohol contained in the decolored reaction mixture was removed to a level of 1% (as determined by GLC analysis) at 160° C. and 0.3 mmHg using a thin-film evaporator. The alkylglycoside obtained was dissolved in distilled water to make a 40% by weight alkylglycoside aqueous solution. This aqueous solution had a good color of APHA 200 (G1) and no odor. NMR analysis of the obtained alkylglycoside revealed that the average degree of glucose condensation was 1.35.

Example 2

The same procedures as in Example 1 were followed to obtain alkylglycoside except that the pH after decoloration was adjusted to 5.0 by reducing the amount of acid solution. The 40% by weight aqueous solution of the alkylglycoside obtained has a good color of APHA 200 to 250 (G1 to 2) and no odor. The average degree of glucose condensation was 1.35.

Example 3

The same procedures as in Example 1 were followed to obtain alkylglycoside except that pH was adjusted to 6.5 after decoloration by reducing the amount of acid solution. The 40% by weight aqueous solution of the alkylglycoside obtained have a relatively good color of APHA 300 (G2) and no odor. The average degree of glucose condensation was 1.35.

Example 4

To a 2-liter reactor, 734 g (4.0 mol) of a mixture of decyl alcohol, dodecyl alcohol and tetradecyl alcohol (molar ratio=40%:30%:30%; hereinafter referred to as "an alcohol mixture"), 180 g (1.0 mol) of anhydrous glucose, and 0.95 g (0.005 mol) of p-toluenesulfonic acid monohydrate were placed and stirred. After the mixture was heated to 95° C., the pressure in the reaction system was adjusted to 40 mmHg to start dehydration. During the dehydration, nitrogen was introduced into the reactor at a rate of 10 mL/min to efficiently remove the water formed. The mixture was further heated. When the reaction temperature reached 110° C., sampling was repeated every 1 hour to know the amount of glucose consumption. Dehydration was continued until the conversion calculated from the glucose consumption became 96%.

After the completion of the reaction, the pressure was normalized and the catalyst was neutralized by adding 1.17 g (0.014 mol) of 48% by weight NaOH aqueous solution. By-products formed during the reaction, such as polysaccharides, and unreacted glucose, were removed by filtration. The reaction time for dehydration and color of the reaction mixture (APHA 300 to 400) in Example 4 were almost equal to those in Example 1 where decyl alcohol was used as the starting material.

In a 1-liter reactor, 500 g of the reaction mixture (containing alkylglycoside in an amount of about 30% by weight; hereinafter referred to as "the reaction mixture of Example 4") was placed and stirred. After the reaction mixture of Example 4 was heated to 70° C., 1.00 g (0.012 mol) of 48% by weight NaOH aqueous solution and 2.86 g (0.2% by weight $H_2O_2$ to the amount of reaction mixture) of 35% by weight $H_2O_2$ aqueous solution were added and stirred at 70° C. for 3 hours for decoloration. During the decoloration treatment, the reaction mixture was sampled at several points. The sample was diluted to a concentration of 5% by weight and the pH of the dilution was determined. As a result, the pH of the reaction system during the decoloration treatment was in the range of from 11.5 to 8.5. After the completion of the decoloration treatment, the pH of the reaction mixture was adjusted with 7.61 g (0.012 mol) of the acid solution. The reaction mixture had a color of APHA 70, indicating that the reaction mixture had been decolored. pH of the reaction mixture was 3.0. The reaction mixture was further diluted with distilled water to a concentration of 5% by weight, and the pH of the resulting suspension was 3.5.

Unreacted alcohol contained in the above decolored reaction mixture was removed to a level of 1% at 160° C. and 0.3 mmHg using a thin-film evaporator to separate an alkylglycoside. The alkylglycoside obtained was dissolved in distilled water to make a 40% by weight alkylglycoside aqueous solution. This aqueous solution had a good color of APHA 150 to 200 (G1) and no odor. The average degree of glucose condensation of the alkylglycoside obtained was 1.30.

Example 5

In a 1-liter reactor, 500 g of the reaction mixture of Example 1, 1.00 g of 48% by weight NaOH aqueous solution, and 1.91 g (0.05 parts by weight of NaOCl based upon 100 parts by weight of the reaction mixture of Example 1) of 13.1% by weight NaOCl aqueous solution (effective chlorine: 12.5%) as a decoloring agent (in place of $H_2O_2$ used in Example 1) were placed and subjected to the decoloration treatment and pH adjustment according to the same procedures as in Example 1. The reaction system was adjusted to a pH of from 11.5 to 9.0 during decoloration and to a pH of 3.5 after the decoloration. The reaction mixture exhibited a color of APHA 80, indicating that the reaction mixture had been decolored.

In the same manner as in Example 1, an alkylglycoside was separated, and 40% by weight alkylglycoside aqueous solution was prepared. This aqueous solution had a good color of APHA 200 (G1) and no odor. The average degree of glucose condensation of the alkylglycoside obtained was 1.35.

Example 6

The same procedures as in Example 5 were followed to obtain an alkylglycoside except that pH after decoloration was adjusted to 5.0 by reducing the amount of the acid solution. A 40% by weight aqueous solution of the alkylglycoside obtained was prepared. This aqueous solution had a good color of APHA 200 to 250 (G1 to 2) and no odor. The average degree of glucose condensation of the alkylglycoside obtained was 1.35.

Example 7

The same procedures as in Example 5 were followed to obtain an alkylglycoside except that pH after decoloration was adjusted to 6.5 by reducing the amount of the acid solution. A 40% by weight aqueous solution of the alkylglycoside obtained was prepared. This aqueous solution had a good color of APHA 300 (G2) and no odor. The average degree of glucose condensation of the alkylglycoside obtained was 1.35.

Example 8

To a 1-liter reactor, 500 g of the reaction mixture of Example 1, 1.00 g of 48% by weight NaOH aqueous solution, and 0.25 g (as 0.05 parts by weight of NaBH based upon 100 parts by weight of the reaction mixture of Example 1) of sodium borohydride were placed and subjected to the decoloration treatment and pH adjustment by the same procedures as in Example 1. The reaction system was adjusted to a pH of from 11.5 to 8.5 during decoloration and to a pH of 3.5 after the decoloration. The reaction mixture exhibited a color of APHA 120, indicating that the reaction mixture had been decolored.

From the above decolored reaction mixture, an alkylglycoside was separated in the same manner as in Example 1, and 40% by weight alkylglycoside aqueous solution was prepared. This aqueous solution had a good color of APHA 200 to 250 (G1 to 2) and no odor. The average degree of glucose condensation of the alkylglycoside obtained was 1.35.

Example 9

To the 40% by weight alkylglycoside aqueous solution obtained in Example 8, 0.02 parts by weight of $NaBH_4$ based upon 100 parts by weight of the alkylglycoside aqueous solution was added to carry out re-decoloration treatment. Specifically, the same procedures as taken in the decoloration treatment and pH adjustment in Example 1 were followed. The pH was adjusted to be in the range of from 10 to 8 during decoloration. The solution after pH adjustment exhibited a color of APHA 100, indicating that the solution had been decolored.

Example 10

An alkylglycoside was separated and a 40% by weight aqueous solution of the alkylglycoside was prepared, in the same manner as in Example 8 except that the pH after decoloration was adjusted to 5.0 by reducing the amount of acid solution added. The aqueous solution exhibited a good color of APHA 200 to 250 (G1 to 2) and no odor. The average degree of glucose condensation was 1.35.

Example 11

The separation of alkylglycoside and preparation of 40% by weight aqueous solution thereof were carried out in the same manner as in Example 8 except that the pH after decoloration was adjusted to 6.5 by reducing the amount of acid solution added. The aqueous solution exhibited a good color of APHA 300 (G2) and no odor. The average degree of glucose condensation was 1.34.

Comparative Example 1

The separation of alkylglycoside and preparation of 40% by weight aqueous solution thereof were carried out in the same manner as in Example 1 except that the pH after decoloration was adjusted to 1.5 with the acid solution. The aqueous solution exhibited a poor color of APHA 500<(G8). Since the strong unpleasant odor of this aqueous solution indicated degradation of the alkylglycoside, no detailed analysis was not made for the alkylglycoside obtained.

Comparative Example 2

The separation of alkylglycoside and preparation of 40% by weight aqueous solution thereof were carried out in the same manner as in Example 1 except that the pH adjustment after decoloration was not done (i.e., at pH 8.5). The aqueous solution exhibited a poor color of APHA 500<(G6) and a burnt smell. The average degree of glucose condensation was 1.35.

Comparative Example 8

The separation of alkylglycoside and preparation of 40% by weight aqueous solution thereof were carried out in the same manner as in Example 1 except that the pH after decoloration was adjusted to 10.0 with 48% by weight NaOH aqueous solution. The aqueous solution exhibited a markedly poor color of APHA 500<(G10) and a strong burnt smell. The average degree of glucose condensation was 1.35.

Comparative Example 4

The separation of alkylglycoside and preparation of 40% by weight aqueous solution thereof were carried out in the same manner as in Example 5 except that the pH after decoloration was adjusted to 1.5 with the acid solution. The aqueous solution exhibited a poor color of APHA 500<(G8). Since the strong unpleasant odor of this aqueous solution indicated degradation of the alkylglycoside, no detailed analysis of the alkylglycoside obtained was not made.

Comparative Example 5

The separation of alkylglycoside and preparation of 40% by weight aqueous solution thereof were carried out in the same manner as in Example 5 except that the pH adjustment after decoloration was not done (i.e., at pH 9.0). The aqueous solution exhibited a poor color of APHA 500<(G6 to 7) and a burnt smell. The average degree of glucose condensation of the alkylglycoside obtained was 1.35.

Comparative Example 6

The separation of alkylglycoside and preparation of 40% by weight aqueous solution thereof were carried out in the same manner as in Example 5 except that the pH after decoloration was adjusted to 10.0 with 48% by weight NaOH aqueous solution. The aqueous solution exhibited a markedly poor color of APHA 500<(G11) and a strong burnt smell. The average degree of glucose condensation of the alkylglycoside obtained was 1.35.

Comparative Example 7

The separation of alkylglycoside and preparation of 40% by weight aqueous solution thereof were carried out in the same manner as in Example 8 except that the pH after decoloration was adjusted to 1.5 with the acid solution. The aqueous solution exhibited a poor color of APHA 500<(G8). Since the strong unpleasant odor of this aqueous solution indicated degradation of the alkylglycoside, no detailed analysis of the alkylglycoside obtained was not made.

Comparative Example 8

The separation of alkylglycoside and preparation of 40% by weight aqueous solution thereof were carried out in the same manner as in Example 8 except that the pH adjustment after decoloration was not done (i.e., at pH 8.5). The aqueous solution exhibited a poor color of APHA 500<(G6) and a burnt smell. The average degree of glucose condensation of the alkylglycoside obtained was 1.35.

Comparative Example 9

The separation of alkylglycoside and preparation of 40% by weight aqueous solution thereof were carried out in the same manner as in Example 8 except that the pH after decoloration was adjusted to 10.0 with 48% by weight NaOH aqueous solution. The aqueous solution exhibited a poor color of APHA 500<(G10) and a strong burnt smell. The average degree of glucose condensation of the alkylglycoside obtained was 1.35.

Example 12

To 500 g of the reaction mixture of Example 4, 0.21 g (0.33 mmol) of 30% by weight p-toluenesulfonic acid monohydrate solution in the alcohol mixture was added to adjust pH. The pH of this reaction mixture was 3.0. The reaction mixture was diluted with distilled water to make a 5% by weight suspension, and the pH of this suspension was 5.1.

With the above reaction mixture having a pH of 3.0, an alkylglycoside was separated from unreacted alcohol in the same manner as in Example 4. The alkylglycoside obtained was dissolved in distilled water to prepare a 40% by weight alkylglycoside aqueous solution. The solution had a good color of APHA 300 (G2) and no odor. The average degree of glucose condensation of the alkylglycoside obtained was 1.34.

Comparative Example 10

To 500 g of the reaction mixture of Example 4, 0.25 g (3.0 mmol) of 48% by weight NaOH aqueous solution was added to adjust pH. This reaction mixture had a pH of 10.7. The reaction mixture was diluted with distilled water to make a 5% by weight suspension, and the pH of this suspension was 10.0.

With the above reaction mixture having a pH of 10.7, an alkylglycoside was separated from an unreacted alcohol in the same manner as in Example 4. The alkylglycoside obtained was dissolved in distilled water to prepare a 40% by weight alkylglycoside aqueous solution. The solution had a poor color of APHA 500<(G8 to 9) and a burnt smell. The average degree of glucose condensation of the alkylglycoside obtained was 1.42.

Comparative Example 11

The alcohol removal by distillation from the reaction mixture of Example 4 was carried out without adjusting pH. The reaction mixture before distillation of alcohol had a color of APHA 300 to 400 and a pH of 7.0. The reaction mixture was further diluted with distilled water to make a 5% by weight suspension, and the pH of the suspension was 6.8.

With the above reaction mixture having a pH of 7.0, an alkylglycoside was separated from an unreacted alcohol in the same manner as in Example 4. The alkylglycoside obtained was dissolved in distilled water to make a 40% by weight alkylglycoside aqueous solution. This aqueous solution had a poor color of APHA 500<(G4) and a burnt smell. The average degree of glucose condensation of the alkylglycoside obtained was 1.35.

Comparative Example 12

To 500 g of the reaction mixture of Example 4, 0.55 g (0.87 mmol) of 30% by weight p-toluenesulfonic acid monohydrate solution dissolved in the alcohol mixture was added to adjust pH. The pH of the reaction mixture was 0.1. This reaction mixture was diluted with distilled water to make a 5% by weight suspension, and the pH of the suspension was 1.5.

With the above reaction mixture having a pH of 0.1, an alkylglycoside was separated from an unreacted alcohol. The alkylglycoside obtained was dissolved in distilled water to make a 40% by weight alkylglycoside aqueous solution. The solution had a poor color of APHA 500<(G10). From the strong peculiar odor of the solution, degradation of alkylglycoside was suggested.

Example 13

In a 20-liter SUS-reactor, 9497 g (60.0 mol) of decyl alcohol, 2700 g (15.0 mol) of anhydrous glucose, and 14.3 g (0.075 mol) of p-toluenesulfonic acid monohydrate were placed, and stirred. After the mixture was heated to 95° C., the pressure in the reaction system was adjusted to 40 mmHg to start dehydration. During the dehydration, nitrogen was introduced into the reactor at 200 mL/min to efficiently remove the water formed. The mixture was further heated. When the temperature reached 110° C., the reaction mixture was sampled every 1 hour to know the amount of glucose consumption. Dehydration was continued until conversion became 96% or higher. After the completion of the reaction, the pressure was normalized and the catalyst was neutralized by adding 17.5 g (0.21 mol) of 48% by weight NaOH aqueous solution.

The neutralized product was a slurry containing polysaccharide by-products and unreacted glucose. In order to confirm the color of this product, a small amount of the product was filtered and the color of the filtrate was determined to be APHA 300 to 400.

After the neutralization as mentioned above, 500 g of the slurry (containing an alkylglycoside in an amount of about 30% by weight) was placed in a 1-liter reactor and stirred. The slurry was then heated to 70° C., to which 1.00 g (0.012 mol) of 48% by weight NaOH aqueous solution, and 2.86 g of 35% by weight $H_2O_2$ aqueous solution (containing 0.2 parts by weight of $H_2O_2$ based upon 100 parts by weight of the reaction mixture) were added and stirred at 70° C. for 3 hours for decoloration. During decoloration, the mixture was sampled several times, and the sample was diluted to a concentration of 5% by weight for pH determination. The pH of the reaction system during decoloration was in the range of from 11.5 to 8.5.

After the completion of the decoloration treatment, the pH of the mixture was adjusted with 7.61 g (0.012 mol) of the acid solution. The color of the mixture was APHA 70 to 80, indicating that the mixture had been decolored. The pH of the mixture was 3.0. The mixture was further diluted with distilled water to make a 5% by weight suspension, and the pH of the resulting suspension was 3.5.

With the above decolored reaction mixture, an alkylglycoside was separated by removing an unreacted alcohol to a level of 1% (as determined by GLC analysis) at 160° C. and 0.3 mmHg using a thin-film evaporator. The alkylglycoside obtained was dissolved in distilled water to make a 40% by weight alkylglycoside aqueous solution. This aqueous solution had a good color of APHA 200 (G1) and no odor. NMR analysis for the obtained alkylglycoside revealed that the average degree of glucose condensation was 1.35.

Example 14

To a 2-liter reactor, 734 g (4.0 mol) of the alcohol mixture, 180 g (1.0 mol) of anhydrous glucose and 0.95 g (0.005 mol) of p-toluenesulfonic acid monohydrate were placed and stirred. After the mixture was heated to 95° C., the pressure in the reaction system was adjusted to 40 mmHg to start dehydration. During the dehydration, nitrogen was introduced into the reactor at a rate of 10 mL/min to efficiently remove the water formed. The mixture was further heated. When the reaction temperature reached 110° C., sampling was repeated every 1 hour to know the amount of glucose consumption. Dehydration was continued until the conversion calculated from the glucose consumption became 96% or more.

After the completion of the reaction, the pressure was normalized and the catalyst was neutralized by adding 1.17 g (0.014 mol) of 48% by weight NaOH aqueous solution. The neutralized product was a slurry containing by-produced polysaccharides and unreacted glucose. In order to confirm the color of this product, a small amount of the product was filtered and the color of the filtrate was determined to be APHA 300 to 400, which was almost equal to the color obtained in Example 13.

After the neutralization as mentioned above, 500 g of the slurry (containing an alkylglycoside in an amount of about 30% by weight) was placed in a 1-liter reactor and stirred. The slurry was then heated to 70° C., to which 1.00 g (0.012 mol) of 48% by weight NaOH aqueous solution, and 2.86 g of 35% by weight $H_2O_2$ aqueous solution (containing 0.2 parts by weight of $H_2O_2$ based upon 100 parts by weight of the reaction mixture) were added and stirred at 70° C. for 3 hours for decoloration. During decoloration, the reaction mixture was sampled several times, and the sample was diluted to a concentration of 5% by weight for pH determination. The pH of the reaction system during decoloration was in the range of from 11.5 to 8.5. After the completion of the decoloration treatment, the pH of the reaction mixture was adjusted with 7.61 g (0.012 mol) of the acid solution. The reaction mixture had a color of APHA 70, indicating that the reaction mixture had been decolored. The pH of the reaction mixture was 3.0. The reaction mixture was further diluted with distilled water to make a 5% by weight suspension, and the pH of the resulting suspension was 3.5.

With the above decolored reaction mixture, an alkylglycoside was separated by removing an unreacted alcohol to a level of 1% at 160° C. and 0.3 mmHg using a thin-film evaporator. The alkylglycoside obtained was dissolved in distilled water to make a 40% by weight alkylglycoside aqueous solution. This aqueous solution had a good color of APHA 150 to 200 (G1) and no odor. The average degree of glucose condensation of the alkylglycoside obtained was 1.30.

Example 15

In a 500-mL four-neck glass flask, 300 g of the 40% by weight alkylglycoside aqueous solution obtained in Example 1 (with a color of APHA 200) was placed and stirred. The solution was then heated to 45° C., and adjusted to a pH of 10 to 11 with 4.4 g of 4% by weight NaOH aqueous solution. After pH adjustment, 0.6 g of 35% by weight $H_2O_2$ aqueous solution was added and stirred at 45° C. for 2 hours for re-decoloration. After the re-decoloration, the solution had a color of APHA 70 and a pH of 8 to 9, indicating that the solution had been decolored.

Tables 2 and 3 summarize the conditions and the results of the above examples.

TABLE 2

| | Decoloration (Re-decoloration) | | | pH before alcohol removal | 40% by weight alkylglycoside aqueous sol. after alcohol removal | |
|---|---|---|---|---|---|---|
| Examples | Decoloring agent | pH | Color APHA | | Color APHA/G | Odor |
| 1 | $H_2O_2$ | 11.5–8.5 | 70–80 | 3.5 | 200/1 | None |
| 2 | $H_2O_2$ | 11.5–8.5 | 70–80 | 5.0 | 200–250/1–2 | None |
| 3 | $H_2O_2$ | 11.5–8.5 | 70–80 | 6.5 | 300/2 | None |
| 4 | $H_2O_2$ | 11.5–8.5 | 70 | 3.5 | 150–200/1 | None |
| 5 | NaOCl | 11.5–9.0 | 80 | 3.5 | 200/1 | None |
| 6 | NaOCl | 11.5–9.0 | 80 | 5.0 | 200–250/1–2 | None |
| 7 | NaOCl | 11.5–9.0 | 80 | 6.5 | 300/2 | None |
| 8 | $NaBH_4$ | 11.5–8.5 | 120 | 3.5 | 200–250/1–2 | None |
| 9 | $NaBH_4$ | 10–8 | 100 | — | — — | — |
| 10 | $NaBH_4$ | 11.5–8.5 | 120 | 5.0 | 200–250/1–2 | None |
| 11 | $NaBH_4$ | 11.5–8.5 | 120 | 6.5 | 300/2 | None |
| 12 | — | — | — | 5.1 | 300/2 | None |
| 13 | $H_2O_2$ | 11.5–8.5 | 70–80 | 3.5 | 200/1 | None |
| 14 | $H_2O_2$ | 11.5–8.5 | 70 | 3.5 | 150–200/1 | None |
| 15 | $H_2O_2$ | 10–11 | 70 | — | — — | — |

Note) Re-decoloration for Exs. 9 and 15

TABLE 3

| Comparative Examples | Decoloration Decoloring agent | pH | Color APHA | pH before alcohol removal | 40% by weight alkylglycoside sol. aqueous after alcohol removal Color APHA/G | Odor |
|---|---|---|---|---|---|---|
| 1 | $H_2O_2$ | 11.5–8.5 | 70–80 | 1.5 | 500</8 | Peculiar odor |
| 2 | $H_2O_2$ | 11.5–8.5 | 70–80 | 8.5 | 500</6 | Burnt smell |
| 3 | $H_2O_2$ | 11.5–8.5 | 70–80 | 10.0 | 500</10 | Strong burnt smell |
| 4 | NaOCl | 11.5–9.0 | 80 | 1.5 | 500</8 | Peculiar odor |
| 5 | NaOCl | 11.5–9.0 | 80 | 9.0 | 500</6–7 | Burnt smell |
| 6 | NaOCl | 11.5–9.0 | 80 | 10.0 | 500</11 | Strong burnt smell |
| 7 | $NaBH_4$ | 11.5–8.5 | 120 | 1.5 | 500</8 | Peculiar odor |
| 8 | $NaBH_4$ | 11.5–8.5 | 120 | 8.5 | 500</6 | Burnt smell |
| 9 | $NaBH_4$ | 11.5–8.5 | 120 | 10.0 | 500</10 | Strong burnt smell |
| 10 | — | — | — | 10.0 | 500</8–9 | Burnt smell |
| 11 | — | — | — | 6.8 | 500</4 | Burnt smell |
| 12 | — | — | — | 1.5 | 500</10 | Peculiar odor |

The above results show that an alkylglycoside with a good color and no odor can be obtained by the present invention. Also, it was found that alkylglycosides obtained by removing an unreacted alcohol at a pH outside the range of the present invention had a poor color and a strong unpleasant odor.

The present invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for producing an alkylglycoside by a reaction of a saccharide and a monohydric alcohol, the method comprising the steps of:

(a) reacting the saccharide with the monohydric alcohol;

(b) subjecting a reaction mixture containing an unreacted monohydric alcohol and an alkylglycoside obtained in step (a) to decoloration by hydrogen peroxide, sodium hypochlorite or hydrogenation;

(c) adjusting the reaction mixture containing an unreacted monohydric alcohol and an alkylglycoside obtained in step (b) to a pH of 2 to 6.5; and (d) removing the unreacted monohydric alcohol from the reaction mixture by distillation.

2. The method according to claim 1, wherein further decoloration is carried out after the unreacted monohydric alcohol is removed by distillation wherein said decoloration is by hydrogen peroxide, sodium hypochlorite treatment or hydrogenation.

3. The method according to claim 1, wherein the alkylglycoside is represented by the following formula (I):

$$R_1(OR_2)_xG_y \quad (I)$$

wherein $R_1$ represents a linear or branched alkyl group having 1 to 22 carbon atoms, a linear or branched alkenyl group having 2 to 22 carbon atoms, or a linear or branched alkylphenyl group having 7 to 22 carbon atoms; $R_2$ represents an alkylene group having 2 to 4 carbon atoms; G represent a residue derived from a reducing saccharide having 5 to 6 carbon atoms; x is a molar addition number of alkylene oxide group, having an average value of from 0 to 5; y is condensation degree of reducing saccharide having an average value of from 1 to 10.

4. The method according to claim 1, wherein the monohydric alcohol is a linear or branched, saturated or unsaturated alcohol having 1 to 22 carbon atoms, or an alkylene oxide addition product thereof, or a mixture thereof.

5. The method according to claim 1, wherein an acidic substance or a basic substance is used to adjust the reaction mixture to a pH of from 2 to 6.5, the acidic substance or the basic substance being soluble in the reaction mixture when used in an amount required to adjust the pH of the reaction mixture within the above range.

6. The method according to claim 1, wherein the hydrogen peroxide treatment is carried out at a pH of from 7 to 13.

7. The method according to claim 1, wherein the sodium hypochlorite treatment is carried out at a pH of from 7 to 13.

8. The method according to claim 1, wherein the hydrogenation treatment is carried out at a pH of not lower than 8.

9. The method according to claim 1, wherein pH is adjusted to a range of from 3.5 to 5 in step (c).

10. The method according to claim 3, wherein $R_1$ is a linear or branched alkyl group having 8 to 16 carbon atoms, and the saccharide is glucose.

11. The method according to claim 5, wherein the acidic substance is selected from the group consisting of p-toluenesulfonic acid, sulfuric acid, phosphoric acid, lactic acid, acetic acid, glycolic acid and hydrochloric acid, and wherein the basic substance is selected from the group consisting of NaOH, KOH, $NH_3$, $Na_2CO_3$, $NaHCO_3$, lower alkyl amines, and lower alkanol amines.

12. The method according to claim 6, wherein pH is adjusted with a basic substance selected from the group consisting of NaOH, KOH, $Na_2CO_3$, $NaHCO_3$, $NH_3$, lower alkanol amines, lower alkyl amines, and strongly basic ion exchange resins.

13. The method according to claim 7, wherein pH is adjusted with a basic substance selected from the group consisting of NaOH, KOH, $Na_2CO_3$, $NaHCO_3$, $NH_3$, lower alkanol amines, lower alkyl amines, and strongly basic ion exchange resins.

14. The method according to claim 8, wherein pH is adjusted with a basic substance selected from the group consisting of NaOH, KOH, $Na_2CO_3$, $NaHCO_3$, $NH_3$, lower alkanol amines, lower alkyl amines, and strongly basic ion exchange resins.

* * * * *